US011636628B2

(12) United States Patent
Rakshit et al.

(10) Patent No.: US 11,636,628 B2
(45) Date of Patent: Apr. 25, 2023

(54) COMPOSITE IMAGERY RENDERING IN DIMINISHED REALITY ENVIRONMENT FOR MEDICAL DIAGNOSIS

(71) Applicant: International Business Machines Corporation, Armonk, NY (US)

(72) Inventors: Sarbajit K. Rakshit, Kolkata (IN); John M. Ganci, Jr., Raleigh, NC (US); James E. Bostick, Cedar Park, TX (US); Martin G. Keen, Cary, NC (US)

(73) Assignee: International Business Machines Corporation, Armonk, NY (US)

( * ) Notice: Subject to any disclaimer, the term of this patent is extended or adjusted under 35 U.S.C. 154(b) by 258 days.

(21) Appl. No.: 16/864,962

(22) Filed: May 1, 2020

(65) Prior Publication Data

US 2021/0343049 A1 Nov. 4, 2021

(51) Int. Cl.
*G06T 11/00* (2006.01)
*A61B 5/00* (2006.01)
(Continued)

(52) U.S. Cl.
CPC ............ *G06T 11/00* (2013.01); *A61B 5/0077* (2013.01); *A61B 5/055* (2013.01); *A61B 6/032* (2013.01);
(Continued)

(58) Field of Classification Search
CPC ....... A61B 5/0077; A61B 5/055; A61B 6/032; A61B 6/037; A61B 6/5235; A61B 6/5247;
(Continued)

(56) References Cited

U.S. PATENT DOCUMENTS 5,546,943 A 8/1996 Gould
6,425,764 B1 7/2002 Lamson
(Continued)

FOREIGN PATENT DOCUMENTS

WO WO2013054257 A1 4/2013
WO WO2018094479 A2 5/2018

OTHER PUBLICATIONS

Ienaga et al., "First Deployment of Diminished Reality for Anatomy Education," 2016 IEEE International Symposium on Mixed and Augmented Reality Adjunct Proceedings, IEEE Computer Society, p. 294-296 (Year: 2016).*
(Continued)

*Primary Examiner* — Sing-Wai Wu
(74) *Attorney, Agent, or Firm* — Kristofer Haggerty; Michael J. Chang, LLC

(57) ABSTRACT

Techniques for composite imagery rendering in a diminished reality environment for medical diagnosis are provided. In one aspect, a method for composite image rendering in a diminished reality environment for medical diagnosis includes: analyzing medical imagery scans for a patient visiting a medical office for consultation with a physician for a diagnosis; obtaining real-time images of the patient who is physically located in the medical office; creating a composite image of the patient comprising relevant portions of the medical imagery scans combined with the real-time images of the patient; selecting one or more portions of the composite image to diminish for the diagnosis; and rendering the composite image in a diminished reality environment.

18 Claims, 6 Drawing Sheets

(51) Int. Cl.

| | | |
|---|---|---|
| *A61B 5/055* | (2006.01) | |
| *A61B 6/03* | (2006.01) | |
| *A61B 6/00* | (2006.01) | |
| *G06K 9/62* | (2022.01) | |
| *G06T 7/00* | (2017.01) | |
| *G16H 30/40* | (2018.01) | |
| *G16H 50/20* | (2018.01) | |
| *G16H 50/70* | (2018.01) | |
| *G16H 30/20* | (2018.01) | |
| *G06V 40/10* | (2022.01) | |
| *A61B 90/00* | (2016.01) | |

(52) U.S. Cl.
CPC ............ *A61B 6/037* (2013.01); *A61B 6/5235* (2013.01); *A61B 6/5247* (2013.01); *A61B 6/5294* (2013.01); *G06K 9/6267* (2013.01); *G06T 7/0014* (2013.01); *G06V 40/10* (2022.01); *G16H 30/20* (2018.01); *G16H 30/40* (2018.01); *G16H 50/20* (2018.01); *G16H 50/70* (2018.01); *A61B 2090/364* (2016.02); *G06T 2207/10081* (2013.01); *G06T 2207/10088* (2013.01); *G06T 2207/10104* (2013.01); *G06T 2207/10116* (2013.01); *G06T 2207/20212* (2013.01); *G06T 2207/30196* (2013.01); *G06T 2210/41* (2013.01); *G06T 2210/62* (2013.01); *G06V 2201/03* (2022.01)

(58) Field of Classification Search
CPC .... A61B 6/5294; G06K 9/6267; G06V 40/10; G16H 30/20; G16H 30/40; G16H 50/70; G16H 50/20; G06T 11/00; G06T 7/0014
See application file for complete search history.

(56) References Cited

U.S. PATENT DOCUMENTS

| | | | |
|---|---|---|---|
| 10,976,806 B1 * | 4/2021 | Vancamberg | ........ A61B 5/0091 |
| 2013/0245461 A1 | 9/2013 | Maier-Hein et al. | |
| 2015/0187136 A1 | 7/2015 | Grimaud | |
| 2016/0249989 A1 | 9/2016 | Devam et al. | |
| 2017/0109628 A1 | 4/2017 | Gokmen et al. | |
| 2019/0142519 A1 | 5/2019 | Siemionow et al. | |
| 2019/0365252 A1 * | 12/2019 | Fernald | ................ A61B 5/0077 |
| 2020/0111210 A1 * | 4/2020 | Maximo | ................ G06T 7/0014 |
| 2020/0160965 A1 * | 5/2020 | Lyman | .................. G16H 50/20 |

OTHER PUBLICATIONS

Mell et al., "The NIST Definition of Cloud Computing," NIST Special Publication 800-145, Sep. 2011 (7 pages).

Mori et al., "A survey of diminished reality: Techniques for visually concealing, eliminating, and seeing through real objects," IPSJ Transactions on Computer Vision and Applications (Jun. 2017) 9:17 (14 pages).

I. Watts et al. "ProjectDR: augmented reality system for displaying medical images directly onto a patient," In Proceedings of the 23rd ACM Symposium on Virtual Reality Software and Technology (VRST '17). ACM, Article 70, 2 pages, Nov. 2017.

N. Ienaga et al., "First Deployment of Diminished Reality for Anatomy Education," 2016 IEEE International Symposium on Mixed and Augmented Reality Adjust Proceedings (ISMAR—Adjunct), Merida, Sep. 2016, pp. 294-296.

L. De Paolis and G. Aloisio, "Augmented Reality in Minimally Invasive Surgery." In: Mukhopadhyay S.C., Lay-Ekuakille A. (eds) Advances in Biomedical Sensing, Measurements, Instrumentation and Systems. Lecture Notes in Electrical Engineering, vol. 55. Springer, pp. 305-320, 2010.

L. De Paolis and G. Aloisio, "Augmented Reality in Minimally Invasive Surgery," ACHI 2012: The Fifth International Conference on Advances in Computer-Human Interactions, pp. 273-277 (Jan. 2012).

S Habert et al., "Multi-layer Visualization for Medical Mixed Reality." arXiv:1709.08962, Sep. 2017 (6 pages).

* cited by examiner

US 11,636,628 B2

COMPOSITE IMAGERY RENDERING IN DIMINISHED REALITY ENVIRONMENT FOR MEDICAL DIAGNOSIS

FIELD OF THE INVENTION

The present invention relates to diminished reality, and more particularly, to composite imagery rendering in a diminished reality environment for medical diagnosis.

BACKGROUND OF THE INVENTION

Diminished reality is a technique for concealing, eliminating, and seeing through objects in a perceived environment in real-time to diminish the reality. In other words, diminished reality can be considered the conceptual opposite to augmented reality. Namely, augmented reality superimposes virtual objects into the real world to enhance reality. By comparison, diminished reality enables the removal of real-world objects from a user's field of view.

For instance, diminished reality can be employed to visually remove existing objects from a user's field of view when the user is viewing a particular space. In that case, the user can perceive how the space looks without those objects in it. Take for example, a scenario where an architect wants to make modifications to a building such as removing an existing staircase and relocating it to another area. Diminished reality can be used to show the architect how it would look with the staircase removed before any actual physical modifications to the building are made.

Thus, diminished reality is a powerful tool that can be applied in a variety of different applications.

SUMMARY OF THE INVENTION

The present invention provides techniques for composite imagery rendering in a diminished reality environment for medical diagnosis. In one aspect of the invention, a method for composite image rendering in a diminished reality environment for medical diagnosis is provided. The method includes: analyzing medical imagery scans for a patient visiting a medical office for consultation with a physician for a diagnosis; obtaining real-time images of the patient who is physically located in the medical office; creating a composite image of the patient comprising relevant portions of the medical imagery scans combined with the real-time images of the patient; selecting one or more portions of the composite image to diminish for the diagnosis; and rendering the composite image in a diminished reality environment.

A more complete understanding of the present invention, as well as further features and advantages of the present invention, will be obtained by reference to the following detailed description and drawings.

DETAILED DESCRIPTION OF PREFERRED EMBODIMENTS

As described above, diminished reality is the conceptual opposite to augmented reality. Namely, while augmented reality superimposes virtual objects into the real world to enhance reality, diminished reality is a tool that enables the removal of real-world objects from a user's field of view.

Provided herein is system and techniques for use thereof that applies diminished reality in the field of medical diagnosis using visual medical data. Specifically, as will be described in detail below, the present techniques create a composite rendering of medical imagery scans whereby contextually relevant imagery in the scans is mapped to a patient, and contextually irrelevant imagery is diminished using diminished reality.

The medical diagnosis of a patient typically involves a number of different types of medical imagery scans taken of a patient. For instance, by way of non-limiting example, Magnetic Resonance Imaging (MRI) scans show size and distributions of bright and dark areas to determine whether a tissue being scanned is healthy. X-ray imaging shows structures within the body. In x-ray image scans, dense materials such as bone appear white, air in the lungs appears black, while fat and muscles appear gray. Computed tomography (CT) scans use a series of x-rays from different angles to create cross-sectional views of bone, blood vessels, soft tissue, etc. An ultrasound provides images of soft tissue structures and can measure blood flow in blood vessels such as arteries. Positron Emission Tomography (PET) scans use a radioactive tracer and imaging to reveal how tissues and organs are functioning.

Each of these medical imagery scans shows different aspects of a patient's health that must be analyzed collectively for diagnosis. Further, in many cases a physician needs to examine multiple parts of the body one time based on the contextual situation in order to understand how those multiple parts of the body are interacting and working together. Advantageously, the present techniques work to present a diminished reality view of a composite of these medical imagery scans and of the real-life patient to a physician performing a diagnosis of the patient. As will be described in detail below, based on the contextual situation the present system then forecasts which parts of the body need to be examined together and combines the relevant portions of each medical imagery scan into the physician's view, diminishing, removing, and replacing elements of the medical imagery scans and/or real-world patient as needed.

Figure 1:
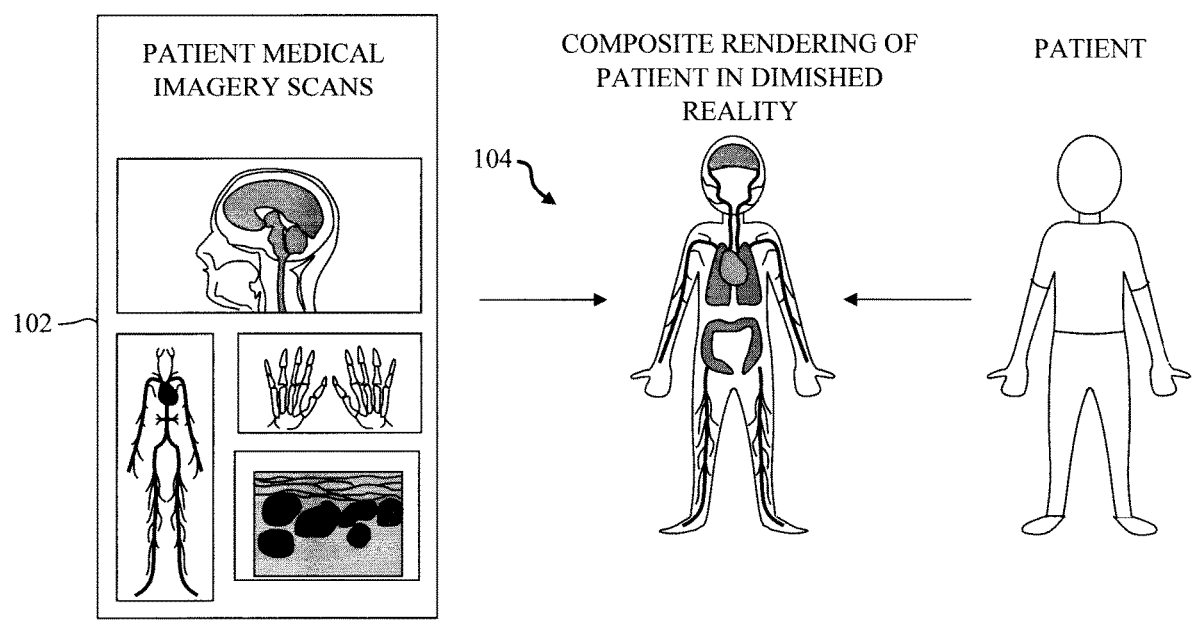
FIG. 1 is a diagram illustrating an exemplary use case where a patient visits a physician to discuss symptoms for the purpose of a medical diagnosis according to an embodiment of the present invention.

An overview of the present techniques is now provided by way of reference to FIG. 1 which illustrates an exemplary use case where a patient visits a physician to discuss symptoms for the purpose of a medical diagnosis. Use of the term 'physician' throughout the instant description is for illustrative purposes only, and it is to be understood that the present system can be used by any medical professional such as a physician or other clinician for the purposes of diagnosis. As highlighted above, the present system renders composite imagery in a diminished reality environment. To do so, the system first retrieves available medical imagery scans 102 from the patient's medical history. As provided above, these medical imagery scans can include, but are not limited to, MRI, x-ray, CT, ultrasound and/or PET scans. More generally, however, the present techniques can leverage (medically-relevant) data from any source that is visual in nature like the above-mentioned scans. To look at it another way, an example of a source that is not visual in nature is a result of a blood test.

It is notable that retrieval of medical imagery scans 102 for the patient can be performed at a time prior to the patient's visit to the physician. For instance, in anticipation of the patient's future appointment, the present system can retrieve all available and relevant medical imagery scans 102 for the patient. For instance, the patient might have medical imagery scans from previous medical evaluations, as might the physician(s) whose performed those evaluations. Further, medical imagery scans might also be present in a central database that can be accessed by the physicians, facility (e.g., hospital, clinic, etc.) treating the patient. Alternatively, the system can retrieve the medical imagery scans 102 at the time of the patient's visit to the physician. In that case, the relevant medical imagery scans retrieved can be based on feedback the patient provides (e.g., regarding a certain condition) during the visit.

During the visit, the patient can provide additional medically-relevant data regarding the diagnosis. For instance, the patient might provide feedback regarding certain symptoms the patient is experiencing. Using this patient feedback data, the system then analyzes the medical imagery scans 102 that have been retrieved for the patient and derives the contextually relevant scans that should be rendered (in a diminished reality environment—see below). For instance, by way of non-limiting example, if the patient feedback focuses on right arm pain, then the system will select those medical imagery scans 102 that are contextually relevant to diagnosing pain in the right arm.

The system will then perform image classification on the patient to correlate parts of the body with patient images. As will be described in detail below, according to an exemplary embodiment this image classification is performed on digital images taken of the patient (patient images) who is present in the medical office using a machine-learning process to correlate parts of the body with the patient images. For instance, by way of non-limiting example, in one exemplary embodiment a convolutional neural network is used to derive which grouping of pixels in the patient images correspond to the patient's left arm, right ear, and so forth.

The system then renders a composite view 104 consisting of portions of the contextually relevant medical imagery scans 102 and real-life patient image in a diminished reality environment. Namely, where obstructions are present from body parts in the real-life patient image or from irrelevant details in the medical imagery scans 102 the system diminishes these objects to provide an unobstructed view of objects of highest importance.

To enable the physician to view the composite view 104 in real-time, according to an exemplary embodiment the physician wears a diminished reality device. The diminished reality device can generally include any wearable device technology that can display the composite view 104 to a user. For instance, by way of example only, suitable diminished reality devices include, but are not limited to, smart goggles, smart contact lenses, smart glasses, etc. With a wearable diminished reality device, the physician can move relative to the patient, or vice versa, to change the view. For instance, as will be described in detail below, the above-described process is repeated by the system when either the patient or the physician moves in space to re-render the composite view 104 (i.e., from a different perspective).

Figure 2:
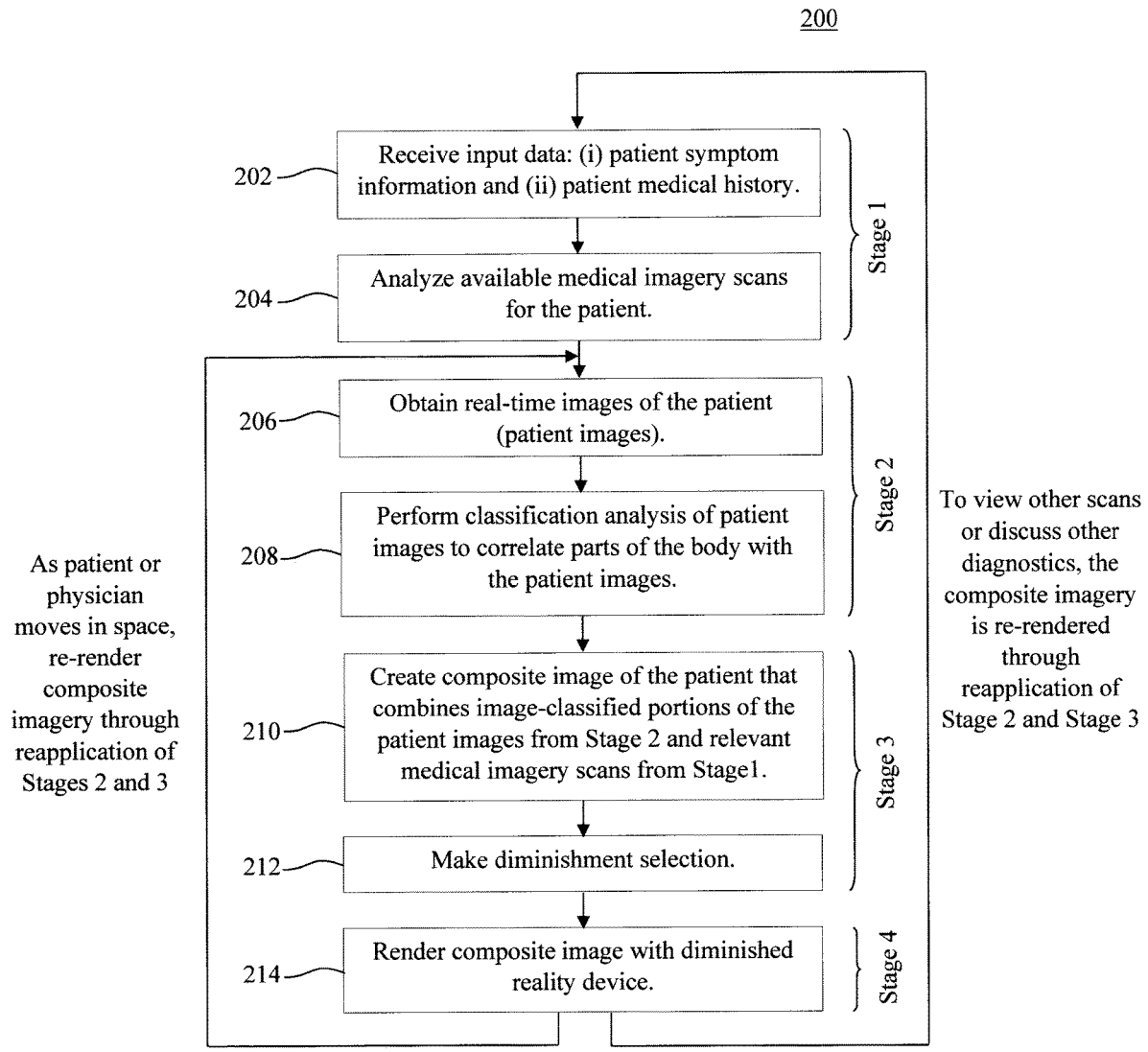
FIG. 2 is a diagram illustrating an exemplary methodology for composite image rendering in a diminished reality environment for medical diagnosis according to an embodiment of the present invention.

Given the above overview, FIG. 2 provides an exemplary methodology 200 for composite image rendering in a diminished reality environment for medical diagnosis in accordance with the present techniques. In a first stage (Stage 1) of methodology 200, a patient visits a medical office for a consultation with a medical professional, such as a physician, for the purposes of a diagnosis, and in step 202 the present system takes as input data (i) patient symptom information and (ii) patient medical history. By way of example only, this input data is provided directly by the doctor and/or patient, and/or indirectly through integration with other medical systems which enables the system to retrieve medical imagery scans from previous medical evaluations.

The patient symptom information can be obtained directly from the patient. For instance, during the visit to the medical office, the patient will tell the physician what symptoms the patient is experiencing. The physician can then enter that information into the system to aid in producing the composite image that is contextually relevant. For instance, using the non-limiting example from above, the patient might have the symptom of right arm pain. For instance, by way of non-limiting example, if the patient provides feedback that mentions right arm pain, the system will select those medical imagery scans, patient images and diminished reality view that are contextually relevant to diagnosing pain in the right arm.

The patient medical history information can generally include any diagnoses, treatments and/or ailments the patient has had in the past. This patient medical history information can be helpful in making the current medical diagnosis. For instance, a prior injury to the patient's right arm might be germane to diagnosing a current pain in the right arm. The patient medical history information can be retrieved from a variety of different sources such as directly from the physician and/or from the patient, or indirectly from integration with other medical systems which enables the system to retrieve medical history data.

In step 204, the system analyzes the available medical imagery scans 102 for the patient. For instance, according to an exemplary embodiment described in detail below, the system can access patient medical imagery scan corpora containing the medical imagery scans 102 for the patient. These medical imagery scans 102 can be obtained directly from the physician and/or from the patient, and/or indirectly from a database(s) of available images from which the system can retrieve the images.

In general, the medical imagery scans 102 can include any source of (medically-relevant) information for the patient that is visual in nature. For instance, by way of example only, the medical imagery scans 102 can include at least one of an MRI, x-ray, CT, ultrasound and/or PET scan of the patient. Further, if already available, any of the data obtained in step 202 and/or step 204 can optionally be retrieved by the system before the patient's visit to the medical office. For instance, in anticipation of the patient's future appointment, any available patient symptom/patient medical history and contextually relevant medical imagery scans 102 for the patient can be retrieved ahead of time. For instance, the patient can provide some information regarding potential symptoms and give a medical history prior to the visit.

Alternatively, some or all of the data can be obtained in step 202 and/or step 204 during the patient's visit to the medical office.

According to an exemplary embodiment, the analysis performed in step 204 involves correlating the patient symptoms and medical history (retrieved in step 202—see above) to the most contextually relevant medical imagery scans 102 available. By this process, a selection is made as to which medical imagery scans 102 (e.g., MRI, x-ray, CT, ultrasound and/or PET scans) will be relevant to the physician for diagnostic purposes. For instance, using the above example as an illustration, given a medical history indicating a past injury to the patient's right arm, and the symptoms of having pain in the right arm, then the analysis performed in step 204 might indicate that the medical imagery scans 102 of the patient's right arm and surrounding areas might be relevant to the diagnosis. Further, the link between symptoms and medical history and contextual relevancy of medical scans can be made through analysis of derived physician preference (for example in prior cases of symptom X with medical history Y which medical scans has a physician requested?). This can also be determined through a simple lookup table that correlates symptoms to medical imagery scans.

In a second stage (Stage 2) of methodology 200, a classification of patient image captures is performed. As highlighted above, this classification process serves to correlate parts of the patient's body to render along with the relevant medical imagery scans 102 to produce the composite image. For instance, in step 206 images are obtained of the patient (i.e., patient images) who is physically located in the medical office. In other words, these patient images are taken in real-time (i.e., real-time images of the patient). According to an exemplary embodiment, these real-time patient images are obtained using a streaming camera or set of camera devices configured to capture digital still and/or digital video images of the patient. As is generally known in the art, a digital image is composed of a collection of digital image elements or pixels. Each pixel has associated therewith a numeric representation of its intensity or gray level.

As will be described in detail below, new patient images are obtained whenever the patient or medical professional moves in space in order to re-render the composite image from a different view. Thus, according to an exemplary embodiment, each of the patient images is taken from a particular view. In that regard, the system should consider patient orientation to the camera to align patient position with the composite image and re-render the composite image using updated patient images if the patient or physician adjusts position to a different view.

In step 208, a classification analysis of the patient images is performed to correlate the patient images with particular parts of the patient. According to an exemplary embodiment, this classification analysis is performed using a machine-learning process. For instance, in one exemplary embodiment a convolutional neural network is used to derive which grouping of pixels in the patient images correspond to a particular part of the patient such as the patient's left arm, right ear, and so forth.

In machine learning and cognitive science, neural networks are a family of statistical learning models inspired by the biological neural networks of animals, and in particular the brain. Neural networks may be used to estimate or approximate systems and cognitive functions that depend on a large number of inputs and weights of the connections which are generally unknown.

Figure 3:
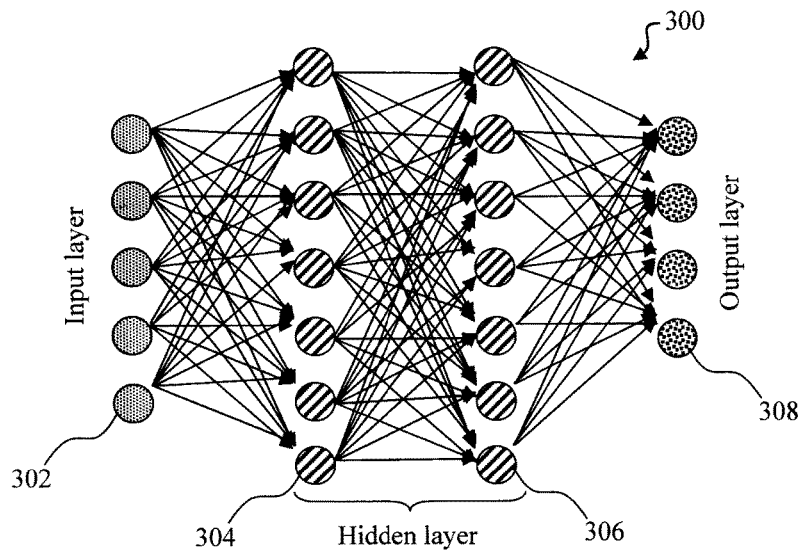
FIG. 3 is a diagram illustrating an exemplary convolutional neural network according to an embodiment of the present invention.

Neural networks are often embodied as so-called "neuromorphic" systems of interconnected processor elements that act as simulated "neurons" that exchange "messages" between each other in the form of electronic signals. Referring briefly to FIG. 3, a schematic illustration of an exemplary convolutional neural network 300 is provided. As shown in FIG. 3, convolutional neural network 300 includes a plurality of interconnected processor elements 302, 304/306 and 308 that form an input layer, at least one hidden layer, and an output layer, respectively, of the convolutional neural network 300.

Similar to the so-called "plasticity" of synaptic neurotransmitter connections that carry messages between biological neurons, the connections in a neural network that carry electronic messages between simulated neurons are provided with numeric weights that correspond to the strength or weakness of a given connection. The weights can be adjusted and tuned based on experience, making neural networks adaptive to inputs and capable of learning. For example, a neural network for image classification is defined by a set of input neurons (see, e.g., input layer 302 in convolutional neural network 300) which may be activated by the pixels of input images, e.g., patient images, medical imagery scans 102, etc. After being weighted and transformed by a function determined by the network's designer, the activations of these input neurons are then passed to other downstream neurons, which are often referred to as "hidden" neurons (see, e.g., hidden layers 304 and 306 in convolutional neural network 300). This process is repeated until an output neuron is activated (see, e.g., output layer 308 in convolutional neural network 300). The activated output neuron determines what image was read.

Instead of utilizing the traditional digital model of manipulating zeros and ones, neural networks create connections between processing elements that are substantially the functional equivalent of the core system functionality that is being estimated or approximated. For example, IBM's SyNapse computer chip is the central component of an electronic neuromorphic machine that attempts to provide similar form, function and architecture to the mammalian brain. Although the IBM SyNapse computer chip uses the same basic transistor components as conventional computer chips, its transistors are configured to mimic the behavior of neurons and their synapse connections. The IBM SyNapse computer chip processes information using a network of just over one million simulated "neurons," which communicate with one another using electrical spikes similar to the synaptic communications between biological neurons. The IBM SyNapse architecture includes a configuration of processors (i.e., simulated "neurons") that read a memory (i.e., a simulated "synapse") and perform simple operations. The communications between these processors, which are typically located in different cores, are performed by on-chip network routers.

By way of example only, a neural network can be embodied in an analog cross-point array of resistive devices. For an exemplary configuration of the resistive devices see, for example, the resistive processing units (RPUs) described in U.S. Patent Application Publication Number 2017/0109628 by Gokmen et al., entitled "Resistive Processing Unit," the contents of which are incorporated by reference as if fully set forth herein.

In a third stage (Stage 3) of methodology 200, a composite view 104 of the patient is created including contextually relevant portions of the medical imagery scans 102 and patient images, and diminishment selection is made. Basically, at this stage the medical imagery scans 102 and patient images are combined into a composite view, and selections are made as to what objects in the composite view will be concealed, eliminated, made see-through, etc. using diminished reality. For instance, where obstructions are present from body parts in the patient images or from irrelevant details in the medical imagery scans 102, the system diminishes these objects to provide an unobstructed view of objects of highest importance for diagnosis.

Specifically, in step 210 the system creates a composite image (i.e., composite view 104) of the patient that combines both: a) the image-classified portions of the patient images (from Stage 2) and b) the contextually relevant medical imagery scans 102 (from Stage 1). According to an exemplary embodiment, a machine-learning process is employed to perform this composite pairing of the patient images and medical imagery scans. For instance, to use an illustrative, non-limiting example, a convolutional neural network (such as neural network 300 of FIG. 3) is used to pair an MRI scan(s) (medical imagery scans 102) of the patient's right arm with the real-time patient image of the patient's right arm as captured by the streaming camera.

In step 212, the system makes a diminishment selection whereby the system selects which portion(s) of the composite image to diminish or in some other way modify to better aid in diagnosis by the physician. For instance, by way of example only, in step 212 one or more objects in the composite image can be diminished while still retaining the object(s) as a frame of reference. To use a non-limiting illustrative example, the translucency of an internal organ can be increased to better illustrate another organ that is obscured from view. Take for instance the example from above involving pain in the right arm. The organs and tissue overlying bone may already have some translucency in the medical imagery scans 102. However, for example, the translucency of the muscles of the right arm can be increased to better illustrate the underlying bone structure. Although translucent, the muscle structure will remain visible in the composite image as a frame of reference.

Additionally, in step 212 objects can be further diminished or removed altogether from the imagery if they are not relevant to the diagnosis. For instance, images of the skin in one section of the right arm can be removed from the imagery altogether to provide an unobstructed view of the underlying bone structure and the (optionally) translucent muscle structure as a frame of reference.

The selection of what portion(s) of the composite image to diminish in the composite image can be based on the patient symptom history and/or patient medical history data. See step 202 above. For instance, if the symptom is that the patient is experiencing pain in the right arm, it may be determined by the system that the medically relevant objects for the physician to use in diagnosing pain in the right arm are images of the bones in the right arm. Thus, other objects such as muscle, skin, etc. overlying the bones can be diminished in the composite image. Additionally, the selection of what portion(s) of the composite image to diminish in the composite image can also be based on feedback from the physician. For instance, the physician or medical professional can provide feedback to the system as to what specific parts of the body they would like to see in order to make a diagnosis. The system can then conceal, eliminate, and/or make see-through other objects (e.g., skin, muscle, etc.) that overlies those specific body parts.

In a fourth stage (Stage 4) of methodology 200, the composite image is rendered in a diminished reality environment. Rendering means generating the composite image that was created in Stage 3 (see above). For instance, according to an exemplary embodiment, the physician wears a diminished reality device and looks at the patient who is physical located in their medical office, and in step 214 the diminished reality device renders the composite image that was created in Stage 3 (see above). As provided above, suitable diminished reality devices can include, but are not limited to, smart goggles, smart contact lenses and/or smart glasses.

According to an exemplary embodiment, this composite image viewed by the physician and/or other medical professional includes a physical view of the patient from the patient images (Stage 2) and the contextually relevant medical imagery scans 102 (Stage 1) overlaid onto the patient images, whereby the composite image is diminished to include only the information medically relevant to making the diagnosis. To look at it another way, objects that are not relevant to diagnosing the patient's symptoms are diminished (i.e., concealed, eliminated, made see-through, etc.) in the composite image. As provided above, the system can determine what is relevant to a diagnosis based on the patient symptom history and/or patient medical history data, as well as from feedback provided by the physician.

As shown in FIG. 2, the composite image is re-rendered whenever the patient and/or physician moves in space. Namely, as provided above, the physician is looking at the patient through a wearable diminished reality device. During the examination, the physician might ask the patient to move in order to have a different view. Likewise, the physician can also move relative to the patient to obtain different views. In either case, because of this movement the physician is looking at a different view of the patient, and as such updated imagery and classification analysis are needed. To do so, Stage 2 and Stage 3 are repeated to obtain updated real-time patient images (using a streaming camera or set of camera devices) from the new view (step 206), perform classification analysis of the updated real-time patient images to correlate parts of the body with the updated real-time patient images (step 208), create a composite image (step 210) and make a diminishment selection (step 212). Each of these steps was described in detail above.

As such, the system can equate the part of the body currently being viewed (via the diminished reality device worn by the physician) with that same part of the composite image. For instance, according to an exemplary embodiment, the convolutional neural network (such as convolutional neural network 300 of FIG. 3—see above) interprets a cluster of pixels into a larger form. For example, a cluster of pixels in the patient image represents the hand of a person, and that the pixels in a medical X-ray image show the skeletal structure of a hand. Thus, one overlays the other.

As also shown in FIG. 2, if the physician wants to view other scans or discuss other diagnostics, the composite imagery is re-rendered through reapplication of Stage 1-Stage 3. This enables the system to obtain the (i) patient symptom information and (ii) patient medical history data pertinent to a different diagnosis (step 102) and analyze the available medical imagery scans 102 for the patient that are medically relevant to that other diagnosis. For instance, to use an illustrative, non-limiting example, one iteration of the process may be performed to render the composite imagery necessary for diagnosing pain in the patient's right arm. To then perform diagnostics on an abdominal pain of the patient, updated symptom information and medical history from Stage 1, along with the updated imagery and classification analysis from Stage 2 and Stage 3 are needed to produce composite imagery for diagnosing the abdominal pain.

As will be described below, one or more elements of the present techniques can optionally be provided as a service in a cloud environment. For instance, by way of example only, the inputs such as the medical imagery scans, patient records, etc. can reside remotely on a cloud server. Also, the composite image processing can be performed on a dedicated cloud server to take advantage of high powered CPUs and GPUs to complete the composite rendering remotely, then send that rendering back to the local device.

Figure 4:
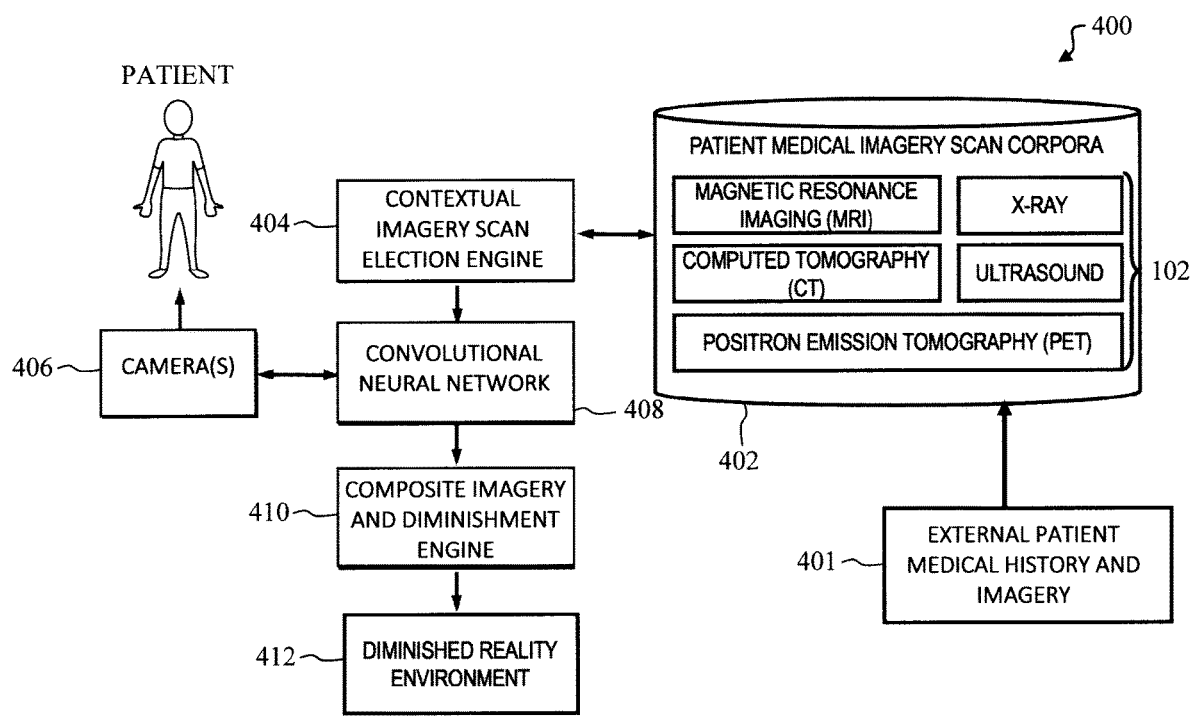
FIG. 4 is a diagram illustrating an exemplary system for composite image rendering in a diminished reality environment for medical diagnosis according to an embodiment of the present invention.

FIG. 4 is a diagram illustrating an exemplary system 400 for composite image rendering in a diminished reality environment for medical diagnosis. By way of example only, system 400 can be implemented in a computer-based apparatus (such as apparatus 500 of FIG. 5—described below) that is configured to perform one or more of the steps of methodology 200 of FIG. 2. For instance, as shown in FIG. 4 system 400 can access external sources 401 of patient data such as patient symptom information and patient medical history input data, and retrieve this patient data as per step 202 of methodology 200. By way of example only, these external sources 401 of patient data can include, but are not limited to, hospital medical records, physician records, etc. As shown in FIG. 4, system 400 includes patient medical imagery scan corpora (e.g., MRI, x-ray, CT, ultrasound and/or PET scans) for the patient present in at least one database 402. As per step 204 of methodology 200, system 400 can retrieve the medical imagery scans 102 for the patient from database 402 and correlate the most contextually relevant scans retrieved with the patient's symptoms and medical history. According to an exemplary embodiment, a contextual imagery scan election engine 404 is present in system 400 for selecting which medical imagery scans 102 retrieved from database 402 will be relevant to the medical professional for diagnostic purposes.

System 400 includes a camera(s) 406 to obtain real-time patient images of the patient who is physically present in the medical office. See step 206 of methodology 200, described above. By way of example only, cameras 406 can include a streaming camera or set of camera devices configured to capture digital still and/or digital video images of the patient.

As shown in FIG. 4, system 400 also includes a convolutional neural network 408 configured, for example, such as the convolutional neural network 300 shown in FIG. 3 and described above. As per step 208 of methodology 200, the convolutional neural network 408 of system 400 can perform classification analysis of the patient images (obtained using camera(s)) 404 to correlate parts of the body with the patient images, e.g., to derive which grouping of pixels in the patient images correspond to the patient's left arm, right ear, and so forth. A composite imagery and diminishment engine 410 then creates a composite image which combines the patient images and the contextually relevant medical imagery scans 102 (as per step 210 of methodology 200) and makes a diminishment selection whereby the system selects which portion(s) of the composite image should be diminished to better aid in diagnosis (as per step 210 of methodology 200). As highlighted above, these actions of the composite imagery and diminishment engine 410 can leverage the convolutional neural network 408.

A diminished reality environment component 412 of system 400 such as a diminished reality device then renders the composite image that was created by the composite imagery and diminishment engine 410 and in step 214 the diminished reality device renders the composite image that was created by the composite imagery and diminishment engine 410 (as per step 214 of methodology 200). As provided above, suitable diminished reality devices include, but are not limited to, smart goggles, smart contact lenses, smart glasses, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 5:
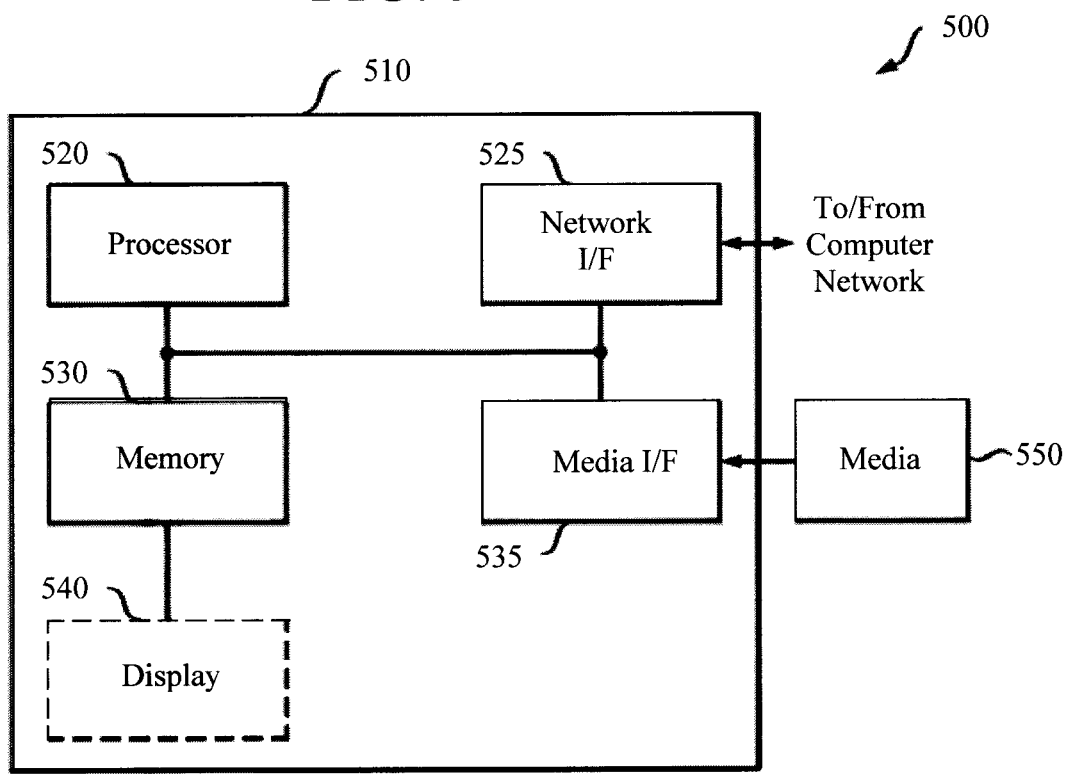
FIG. 5 is a diagram illustrating an exemplary apparatus for performing one or more of the methodologies presented herein according to an embodiment of the present invention.

Turning now to FIG. 5, a block diagram is shown of an apparatus 500 for implementing one or more of the methodologies presented herein. By way of example only, system 400 of FIG. 4 can be implemented in apparatus 500 that is configured to implement one or more of the steps of methodology 200 of FIG. 2.

Apparatus 500 includes a computer system 510 and removable media 550. Computer system 510 includes a processor device 520, a network interface 525, a memory 530, a media interface 535 and an optional display 540. Network interface 525 allows computer system 510 to connect to a network, while media interface 535 allows computer system 510 to interact with media, such as a hard drive or removable media 550.

Processor device 520 can be configured to implement the methods, steps, and functions disclosed herein. The memory 530 could be distributed or local and the processor device 520 could be distributed or singular. The memory 530 could be implemented as an electrical, magnetic or optical memory, or any combination of these or other types of storage devices. Moreover, the term "memory" should be construed broadly enough to encompass any information able to be read from, or written to, an address in the addressable space accessed by processor device 520. With this definition, information on a network, accessible through network interface 525, is still within memory 530 because the processor device 520 can retrieve the information from the network. It should be noted that each distributed processor that makes up processor device 520 generally contains its own addressable memory space. It should also be noted that some or all of computer system 510 can be incorporated into an application-specific or general-use integrated circuit.

Optional display 540 is any type of display suitable for interacting with a human user of apparatus 500. Generally, display 540 is a computer monitor or other similar display.

Figure 6:
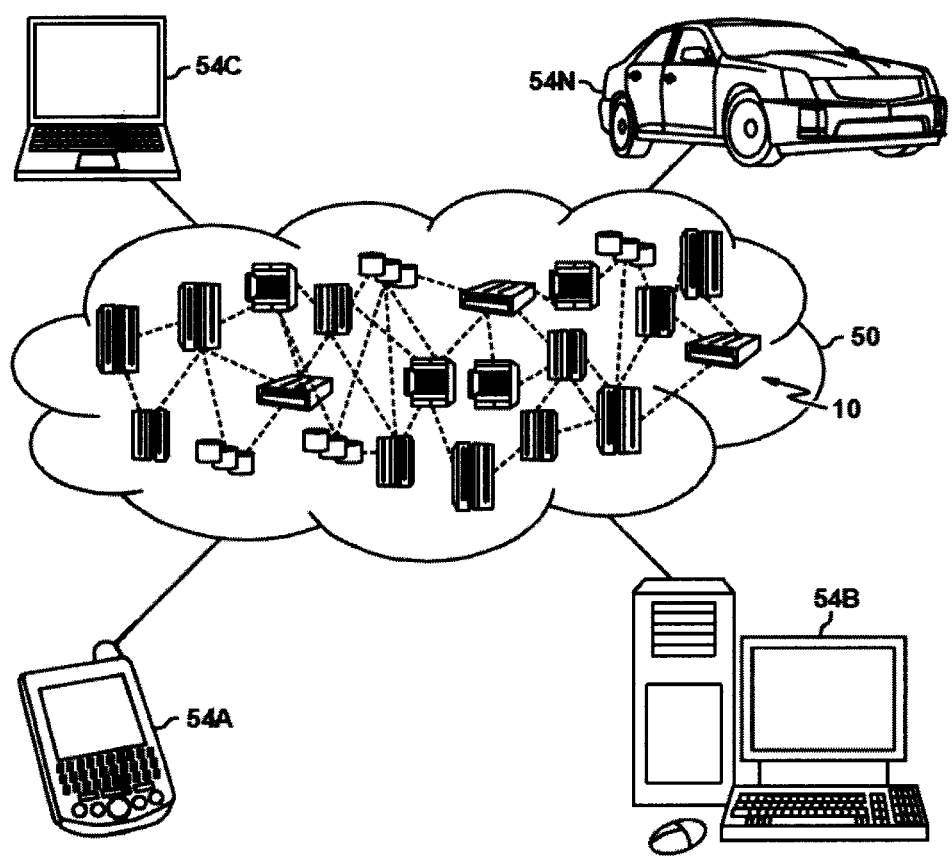
FIG. 6 depicts a cloud computing environment according to an embodiment of the present invention.
Figure 7:
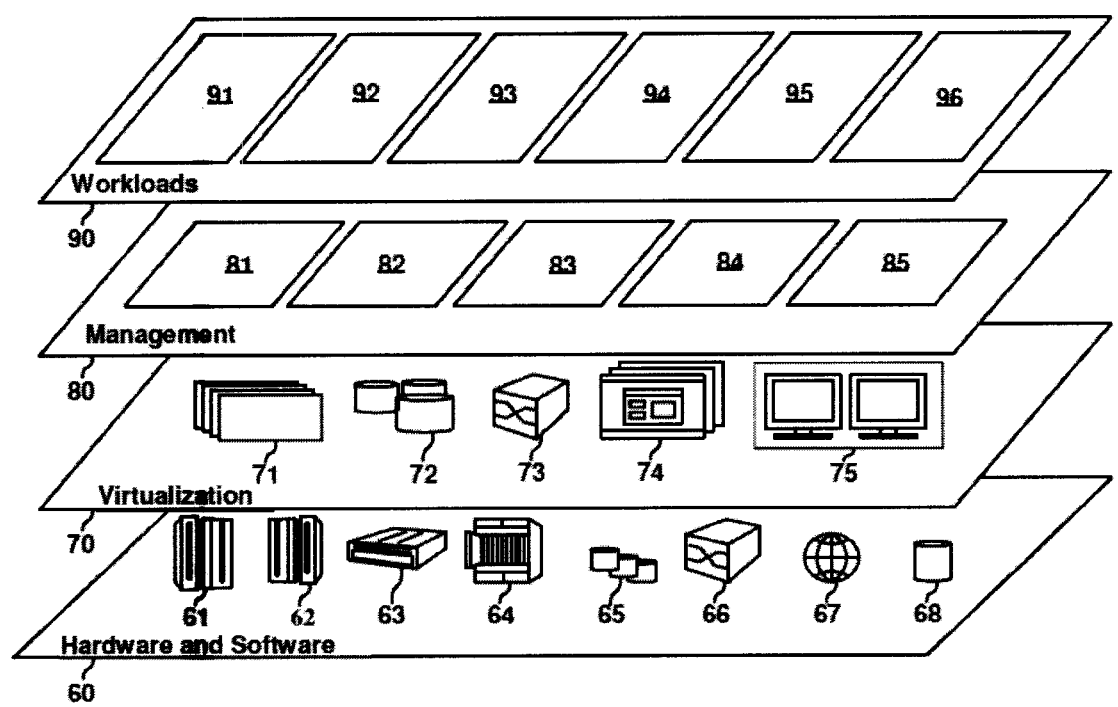
FIG. 7 depicts abstraction model layers according to an embodiment of the present invention.

Referring to FIG. 6 and FIG. 7, it is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 6, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and composite image processing 96.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A method, comprising:
analyzing medical imagery scans for a patient visiting a medical office for consultation with a physician for a diagnosis;
obtaining real-time images of the patient who is physically located in the medical office;
creating a composite image of the patient comprising relevant portions of the medical imagery scans combined with the real-time images of the patient;
selecting one or more portions of the composite image to diminish for the diagnosis; and
rendering the composite image in a diminished reality environment where obstructions are diminished to provide an unobstructed view of underlying objects relevant to the diagnosis, wherein one or more of the obstructions have some translucency in the medical imagery scans, and wherein the translucency of the one or more of the obstructions is further increased in the composite image rendered in the diminished reality environment while still retaining the one or more of the obstructions as a frame of reference.

2. The method of claim 1, wherein the medical imagery scans are selected from the group consisting of: Magnetic Resonance Imaging (MRI) scans, X-ray imaging scans, Computed tomography (CT) scans, Positron Emission Tomography (PET) scans and combinations thereof.

3. The method of claim 1, further comprising:
obtaining (i) patient symptom information and (ii) patient medical history data for the patient.

4. The method of claim 3, wherein analyzing the medical imagery scans for the patient comprises:
correlating the patient symptom information and the patient medical history data to the medical imagery scans to select which of the medical imagery scans are relevant to the physician for the diagnosis.

5. The method of claim 1, further comprising:
performing classification analysis of the real-time images of the patient to correlate the real-time images of the patient with particular parts of the patient.

6. The method of claim 5, wherein the classification analysis of the real-time patient images is performed using a convolutional neural network.

7. The method of claim 6, further comprising:
deriving which grouping of pixels in the real-time patient images correspond to particular parts of the patient using the convolutional neural network.

8. The method of claim 1, wherein the real-time patient images are obtained using a streaming camera or a set of camera devices.

9. The method of claim 1, further comprising:
removing altogether at least one object from the composite image.

10. The method of claim 1, wherein the composite image is rendered in the diminished reality environment using a wearable diminished reality device selected from the group consisting of smart goggles, smart contact lenses, smart glasses, and combinations thereof.

11. The method of claim 1, wherein the composite image that is rendered in the diminished reality environment comprises a physical view of the patient from the real-time images of the patient and the medical imagery scans overlaid onto the real-time images of the patient, wherein the composite image is diminished to include only information relevant to making the diagnosis.

12. The method of claim 1, further comprising the step of:
re-rendering the composite image whenever either the patient or the physician moves in space by repeating the obtaining, the creating, the selecting, and the rendering.

13. A computer program product comprising a computer readable storage medium having program instructions embodied therewith, the program instructions executable by a computer to cause the computer to:
analyze medical imagery scans for a patient visiting a medical office for consultation with a physician for a diagnosis;
obtain real-time images of the patient who is physically located in the medical office;
create a composite image of the patient comprising relevant portions of the medical imagery scans combined with the real-time images of the patient;
select one or more portions of the composite image to diminish for the diagnosis; and
render the composite image in a diminished reality environment where obstructions are diminished to provide an unobstructed view of underlying objects relevant to the diagnosis, wherein one or more of the obstructions have some translucency in the medical imagery scans, and wherein the translucency of the one or more of the obstructions is further increased in the composite image rendered in the diminished reality environment while still retaining the one or more of the obstructions as a frame of reference.

14. The computer program product of claim 13, wherein the program instructions further cause the computer to:
obtain (i) patient symptom information and (ii) patient medical history data for the patient.

15. The computer program product of claim 13, wherein the program instructions further cause the computer to:
perform classification analysis of the real-time images of the patient to correlate the real-time images of the patient with particular parts of the patient.

16. A system comprising a processor, connected to a memory, that is operable to:
analyze medical imagery scans for a patient visiting a medical office for consultation with a physician for a diagnosis;
obtain real-time images of the patient who is physically located in the medical office;
create a composite image of the patient comprising relevant portions of the medical imagery scans combined with the real-time images of the patient;
select one or more portions of the composite image to diminish for the diagnosis; and
render the composite image in a diminished reality environment where obstructions are diminished to provide an unobstructed view of underlying objects relevant to the diagnosis, wherein one or more of the obstructions have some translucency in the medical imagery scans, and wherein the translucency of the one or more of the obstructions is further increased in the composite image rendered in the diminished reality environment while still retaining the one or more of the obstructions as a frame of reference.

17. The system of claim 16, wherein the processor is further operable to:
obtain (i) patient symptom information and (ii) patient medical history data for the patient.

18. The system of claim 16, wherein the processor is further operable to:
    perform classification analysis of the real-time images of the patient to correlate the real-time images of the patient with particular parts of the patient.

\* \* \* \* \*